United States Patent [19]

Wagemann

[11] Patent Number: 4,515,155
[45] Date of Patent: May 7, 1985

[54] INFANT RESTRAINT

[76] Inventor: Dolores Wagemann, 2075 Rialto Ave., San Bernardino, Calif. 92410

[21] Appl. No.: 512,666

[22] Filed: Jul. 11, 1983

[51] Int. Cl.³ .............................................. A61F 13/00
[52] U.S. Cl. .................................. 128/134; 128/87 R; 128/133
[58] Field of Search .......................... 128/87, 133, 134

[56] References Cited

U.S. PATENT DOCUMENTS

| | | | |
|---|---|---|---|
| 2,558,446 | 6/1951 | Lewis | 128/134 |
| 2,785,672 | 4/1957 | Napoli | 128/87 |
| 4,117,840 | 10/1978 | Rasure | 128/134 |

Primary Examiner—John D. Yasko
Assistant Examiner—Christa K. Scott

Attorney, Agent, or Firm—Jack C. Munro

[57] ABSTRACT

A restraint assembly for an infant, and particularly for a premature infant, which takes the form of a shirt or vest which is to cover the torso of the infant from which extends sleeves to be located about each arm of the infant. Each sleeve may include a splint to prevent bending motion at the elbow. The vest includes a closable center opening located across the chest of the infant. A strap is to be securable to each sleeve and is to then be secured to an exterior structure, such as the table on which the infant is located. Leg braces are to be provided which are located about each leg of the infant. Each leg brace will include a removable splint to prevent bending motion at the knee. Securing straps are also to be secured to each leg brace.

4 Claims, 5 Drawing Figures

INFANT RESTRAINT

BACKGROUND OF THE INVENTION

The field of this invention relates to wearing apparel, and more particularly to wearing apparel for use by a newborn, premature infant which restricts the movement of the infant when the infant is connected to a medical apparatus.

Newborn infants are normally placed in a basinette or crib in a comfortably warm environment. Premature infants are normally not clothed. Even though the infant is located in a warm environment, the unclothed infant is subjected to drafts which can cause chills. Premature infants are extremely sensitive and possibly any chill could result in the infant catching a cold which could be quite serious.

Also with premature infants, there is normally a continuous stream of medical procedures required on a daily basis. Examples of these medical procedures are the taking of blood, giving injections and the introduction of an I.V. into the umbilicus of the infant. The insertion of an I.V. within the umbilicus of the infant can be a dangerous procedure. Also, physicians may insert tubes into either the arm or leg of the infant. Further, the tips of the fingers and toes are frequently used in the taking of blood samples.

There is a need for finding adequate means to restrain the infant during the performing of different medical procedures. There is also a need to provide some type of clothing for the infant to supply additional warmth to prevent chilling.

SUMMARY OF THE INVENTION

An infant restraint assembly which is constructed of a plurality of different parts. The main part comprises a vest or shirt, which is to be located about the torso of the infant. The vest is open at the front (down the chest of the infant) so as to facilitate access of I.V. tubes to the umbilicus of the infant, locating of a stethoscope on the chest of the infant and also to facilitate the performing of other medical procedures to the chest and umbilicus of the infant. The vest is integrally connected to a pair of sleeves. An arm of the infant is to be located within each sleeve. Each sleeve includes an elongated pocket within which is removably located a splint to prevent bending of the elbow. Each sleeve includes a fastener assembly to strap the sleeve onto the arm. A securing strap is to be connected to each sleeve which is then secured to the crib or basinette. A leg brace assembly is to be located about each leg of the infant. Each leg brace assembly has a pocket within which is to be located a splint. The splint prevents bending of the leg at the knee. Each leg brace has a fastener assembly to secure the leg brace assembly onto the leg. The leg braces can be connected together in a spaced-apart relationship through a connecting strap. Separate securing straps are to connect with the connecting strap and be located across the leg brace assembly to thereby restrain against movement of the legs of the infant. The vest is to be closable about the open front by means of a separate fastener assembly.

The primary objective of the present invention is to construct a restraint assembly for an infant. In which the extremities of the infant are restrained against movement so as to substantially unhinder the performing of medical procedures upon the infant.

Another objective of this invention is to construct a restraint assembly which further functions as a article of clothing to protect the infant against loss of body heat.

DETAILED DESCRIPTION OF THE SHOWN EMBODIMENT

Figure 1:
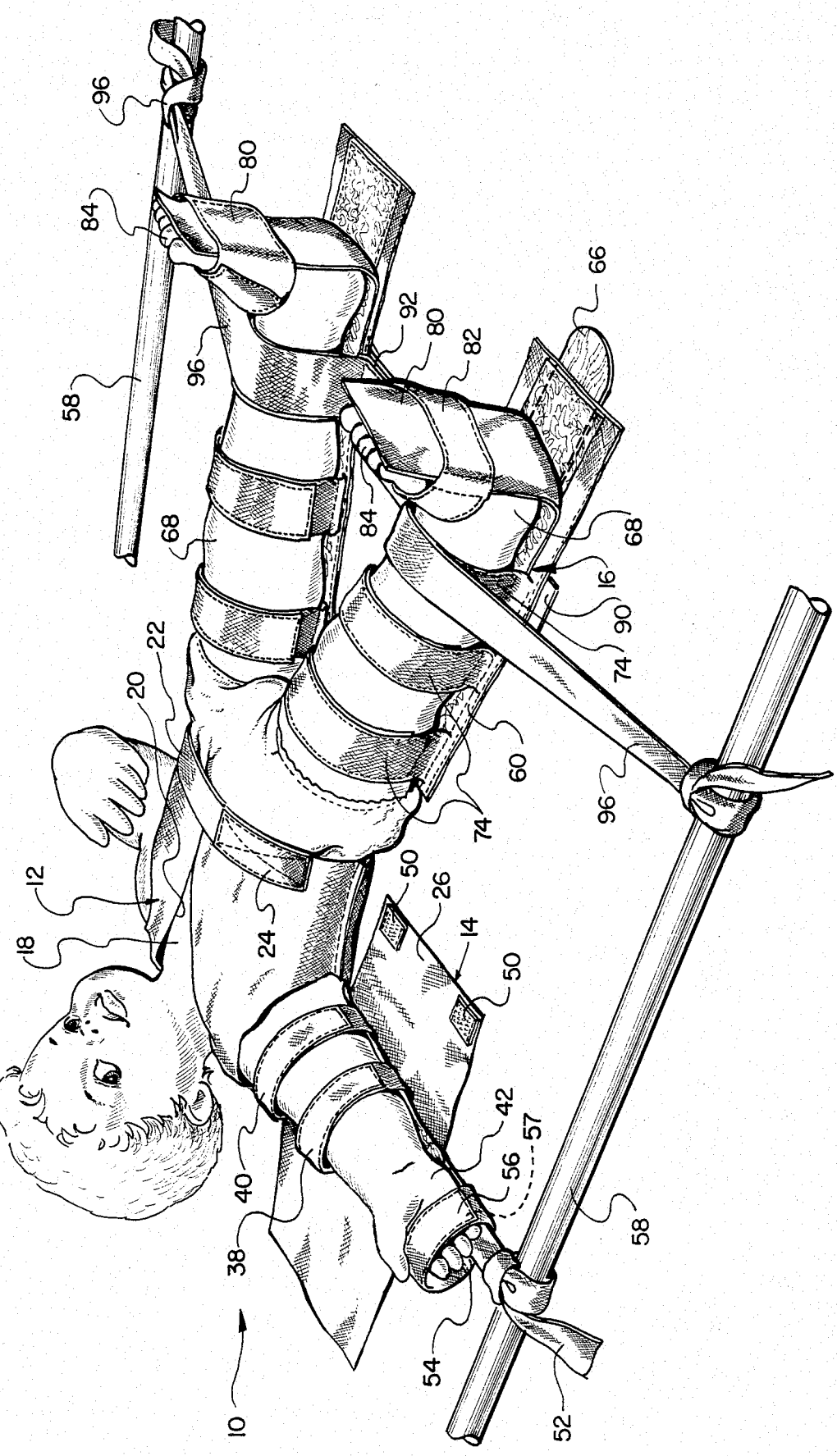
FIG. 1 is an isometric view showing an infant with the infant restraint assembly of the present invention connected to one leg and one arm of the infant.
Figure 2:
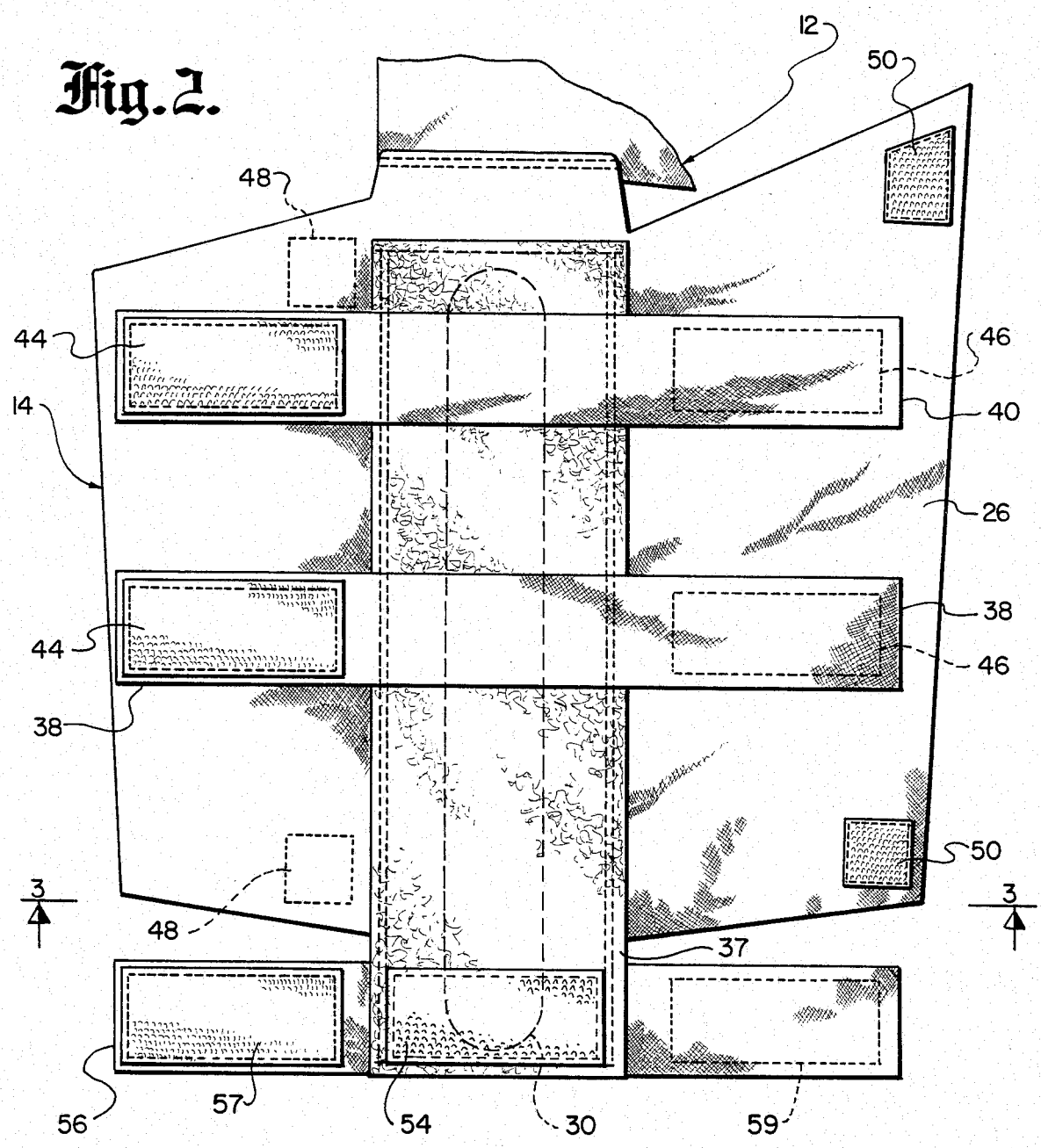
FIG. 2 is a top plan view of a sleeve assembly included within the restraint of this invention showing the sleeve assembly in the open position unsecured to the arm of the infant.
Figure 3:
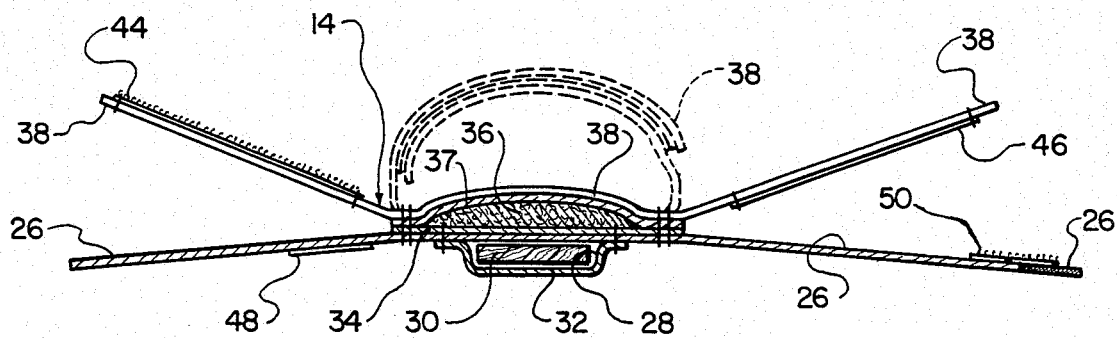
FIG. 3 is a cross-sectional view taken along line 3—3 of FIG. 2.
Figure 4:
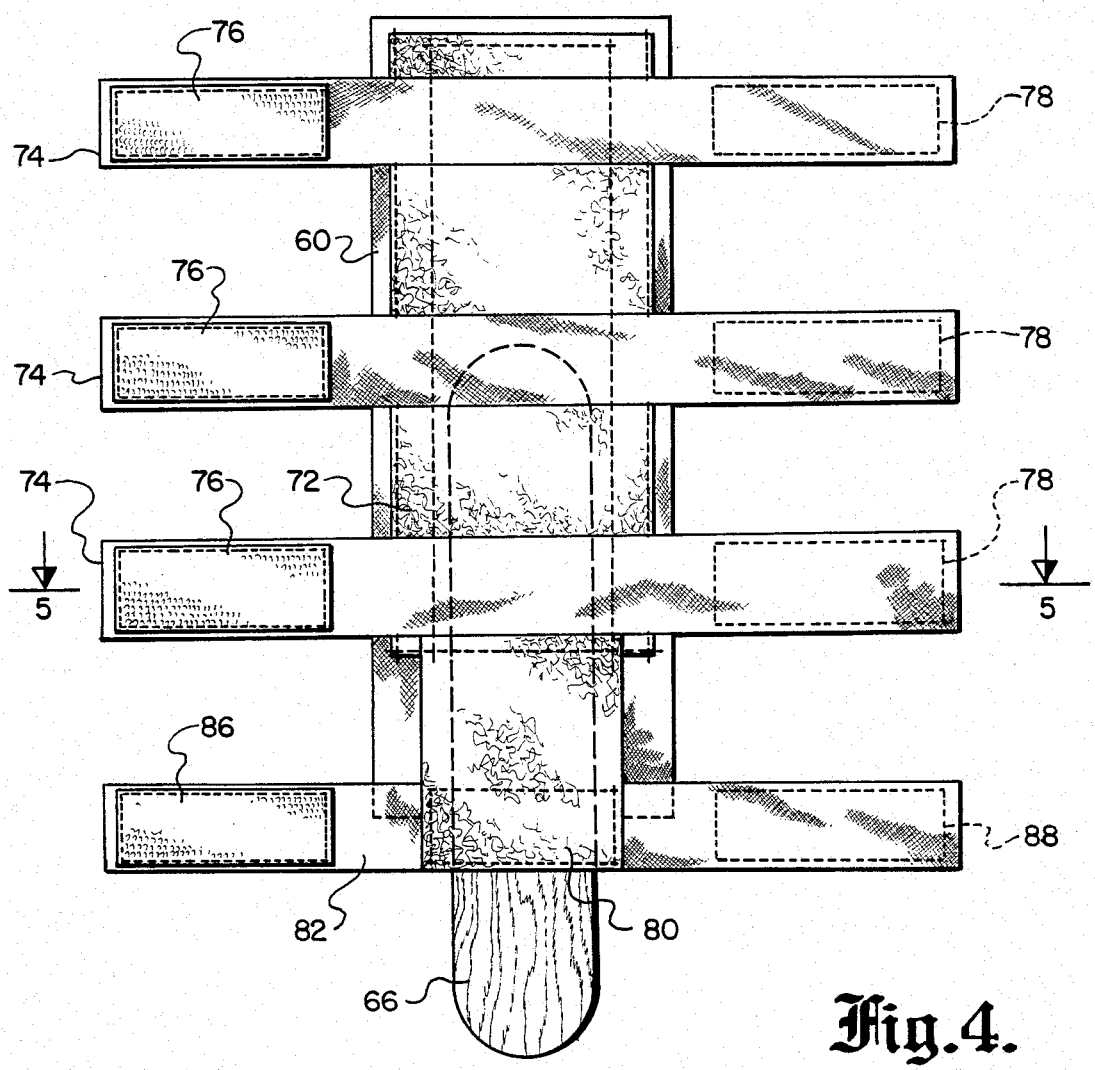
FIG. 4 is a top plan view of a leg brace assembly included within the infant restraint of this invention showing the leg brace assembly in the open position unsecured about the leg of the infant.
Figure 5:
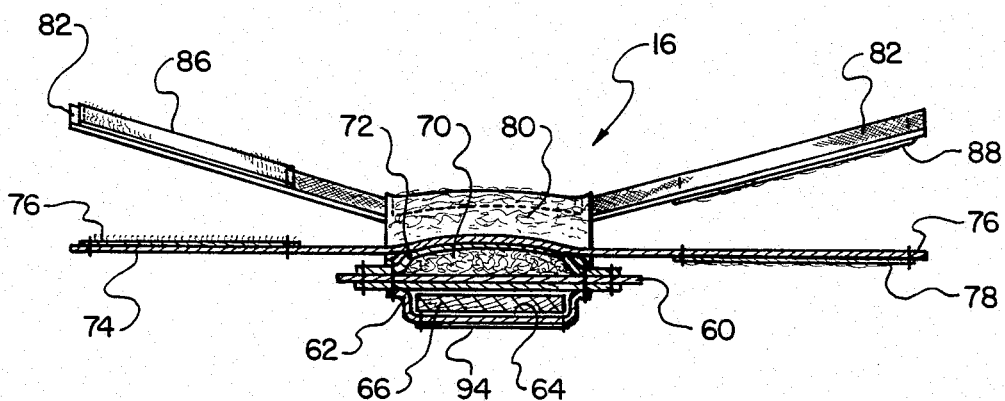
FIG. 5 is an end view of the leg brace assembly taken along line 5—5 of FIG. 4.

Referring particularly to the drawing, there is shown the restraint assembly 10 of this invention which is constructed generally of a vest 12, a sleeve assembly 14 and a leg brace assembly 16. The vest 12 is to be constructed of a fabric material, such as a soft cotton. However, the material of construction is deemed to be whatever is preferable and, in certain instances, the material of construction could be of a nature to facilitate single usage and disposal of the vest. However, normally the fabric will be such that it will be reused and sterilized without incurring any damage.

The vest 12 is constructed to wrap around the torso 18 of the infant. The vest 12 is open at the front or down the torso 18 forming a V-shaped gap 20. A disengageable and re-engageable fastener assembly, composed of strips 22 and 24, are to be utilized to effect holding together of the portions of the vest 12 located on either side of the opening 20. Strip 22 is mounted on the vest 12 on one side of the opening 20, with the strip 24 being attached to the vest 12 on the opposite side of the opening 20. The strip 22 will include a mass of tiny protruding hooks, with the strip 22 including a mass of tiny protruding eyelets. The strip 22 attached to the strip 24 gives an extremely secure connection therebetween. This type of fastener assembly is deemed to be conventional and is normally marketed under the trademark of "Velcro". It is considered to be within the scope of this invention that other desirable types of removable fasteners could be utilized without departing from the scope of this invention.

The sleeve assembly 14 is constructed of an elongated fabric strip 26. The inner end of the strip 26 is attached, as by sewing, to the vest 12. The width of the strip 26 is sufficient so that there are a pair of side flanges which are capable of overlapping each other about the arm of the infant in order to keep the infant as warm as possible.

Mounted on the exterior surface of the strip 26 is a pocket 28. Within the pocket 28 there is to be located a splint 30. Usually the splint 30 will take the form of an elongated strip of wood. The strip 30 is removable from the pocket 28. The pocket 28 is formed by sewing of an outer layer of fabric 32 onto the strip 26.

Attached to the inner surface of the strip 26 is a support layer 34 of fabric. Attached onto the support layer 34 is a quantity of cushioning material 36. Cushioning material 36 will normally take the form of cotton or other cushioning material. It is to be understood that the cushioning material 36 will extend the entire length of the sleeve assembly 14. The cushioning material 36 is covered by a fabric cover 37.

Mounted cross ways on the exterior surface of the fabric cover 37 are a plurality of strips 38 and 40. The length of each of the strips 38 and 40 is such that the ends of each of the strips 38 and 40 are capable of overlapping each other when located about the arm 42 of the infant. The strips 38 and 40 are basically identical. The ends of each of the strips 38 and 40 when overlapped include connecting pads 44 and 46 of the aforementioned hook and eyelet material. It is to be understood that the number of the strips 38 and 40 can vary as well as their location upon the fabric cover 37.

The arm 42 of the infant is to be located against the cushioning material 36. The operator then overlaps the ends of the strips 38 and 40 until the pads 44 and 46 engage in a substantially close fitting arrangement. The operator then proceeds to overlap the side flanges of the strip 26, and when overlapped are connected to hook and eyelet pads 48 and 50.

It may be desirable to attach a securing strap 52 to the sleeve assembly 14 to restrict the arm movement of the infant. The securing strap 52 includes a hook and eyelet pad which in turn is attached to a complementary hook and eyelet pad 54, which is mounted on the outer end of the cover 37. The back of the infant's hand is to be located directly adjacent the pad 54. There is a strip 56 mounted directly adjacent the pad 54 but on the exterior surface of support layer 34. The strip 56 is to be located around the hand of the infant and is held in place by connecting pads 57 and 59. The strip 56 is similar to strip 38 and 40.

The free end of the securing strap 52 is to be wound about and tightly secured to a separate structure, such as a brace member 58 of the basinette or crib. The leg brace assembly 16 is constructed basically similar to the sleeve assembly 14. The leg brace assembly 16 includes a fabric strip 60 to which is attached to the bottom side of lower layer 62 of fabric. The lower layer 62 forms a pocket 64 within which is located a splint 66. Splint 66 is removable, which at times, would be desirable if it is not necessary to prevent bending at the knee of the leg 68 of the infant.

The cushioning material 70 is located against the upper surface of the fabric strip 60. The cushioning material 70 is covered by a cover layer 72 of fabric. Mounted on the cover layer 72 in a spaced-apart relationship are a plurality of strips 74. Each of the strips 74 include cooperating hook and eyelet pads 76 and 78. The pads 76 and 78 are to engage with one another about the leg 68 of the infant. The outer end of the leg brace assembly 16 includes a foot flap 80. Foot flap 80 is free to move in space from the splint 66. A fastening strap 82 is mounted about the foot flap 80 and is adapted to be located about the foot 84 of the infant. The foot strap 82 also includes cooperating hook and eyelet pads 86 and 88.

The function of each leg brace 16 is to prevent each leg from bending at the knee. To further restrain the leg against movement, the leg braces 16 are connected together through a connecting strap 90. Connecting strap 90 has a pair of spaced-apart hook or eyelet pads 92. There is a complementary connecting strip of material 94 which is to connect with pad 92. The strip 94 of one leg assembly 16 connects with one pad 92, with the strip 94 of the other leg assembly 16 connecting with the other pad 92. The connecting strap 90 then functions to prevent further separating movement of the legs 68 of the infant.

To prevent upward movement of each of the legs 68 and also to prevent movement of the legs 68 toward each other, there are utilized a pair of securing straps 96. Each securing strap 96 is basically similar to the strap 52 which includes at the inner end thereof a hook or eyelet pad which in turn connects with the connecting strap 90. The basic material of construction of the connecting strap 90 will be a strip of the hook or eyelet material which will connect with the pad attached to the inner end of each strap 96. One strap 96 then extends over one leg 60, with the other strap 96 extending over the opposite leg and its connected brace assembly 16. The outer end of each of one strap 96 then in turn is fastened to the fixed structure 58 on one side of the infant, with the other strap 96 being secured to the crib or basinette located on the opposite side of the infant.

What is claimed is:

1. In combination for use with an infant, said infant having a torso from which extends a head, legs and arms with a foot connected to each said leg, each said arm terminating in a hand, a restraint assembly for substantially immobilizing an infant, said restraint assembly comprising:

a vest to be located about said torso, said vest including an opening assembly for permitting ease of accessability to the torso, a disengageable first fastener assembly attached to said vest directly adjacent said opening assembly, said first fastener assembly to be operable to connect together said vest about said opening assembly; and at least one sleeve attached to said vest and extending therefrom, a said arm adapted to extend through said sleeve, said sleeve including a first splint, said first splint extending the substantial length of said arm, a second fastener assembly connected to said sleeve, said second fastener assembly to be operable to fixedly secure said sleeve onto said arm, whereby said first splint and said second fastener assembly cooperate to maintain said arm in the extended (non-bent at the elbow) position, said sleeve having a free outer end, said free outer end adapted to be connected with said hand, a third fastener assembly attached to said sleeve at said free outer end, a first securing strap removably connected by said third fastener assembly to said sleeve, whereby said first securing strap is to be connected to a separate structure to restrain against movement said arm located within said one sleeve.

2. The combination as defined in claim 1 wherein:

a first leg brace adapted to be mounted on one said leg, said first leg brace including a second splint, said second splint extending the substantial length of said one said leg, a fourth fastener assembly connected to said first leg brace, said fourth fastener assembly to be operable to fixedly secure said first leg brace onto said one said leg, said first leg brace terminating in a foot flap at its outer end, said foot flap being pivotable relative to said second splint, said foot adapted to connect with said foot flap, whereby said second splint and said fourth fastener assembly cooperating to maintain said one said leg in the extended (non-bent at the knee) position.

3. The combination as defined in claim 2 wherein:
there being a second leg brace adapted to be connected to the other said leg, a connecting strap connected between said first and said second leg braces for preventing spreading apart movement of said legs.

4. The combination as defined in claim 3 wherein:
a second securing strap removably connected to said connecting strap, said second securing strap to be connected to a separate structure to restrain against movement of said one said leg.

* * * * *